United States Patent [19]
Bauer

[11] Patent Number: 5,936,082
[45] Date of Patent: Aug. 10, 1999

[54] METALLOCORRINOIDS AS BIOLOGICALLY COMPATIBLE CARRIERS OF PHARMACOLOGICAL AGENTS

[75] Inventor: Joseph A. Bauer, Akron, Ohio

[73] Assignee: The University of Akron, Akron, Ohio

[21] Appl. No.: 09/000,581

[22] Filed: Dec. 30, 1997

[51] Int. Cl.$^6$ .................................................. C07D 487/22
[52] U.S. Cl. ....................................... 540/145; 536/26.44
[58] Field of Search .............................................. 540/145

[56] References Cited

FOREIGN PATENT DOCUMENTS 10014 of 1990 Japan.
WO 95/31204 11/1995 WIPO.

OTHER PUBLICATIONS

Kaczka et al., *Vitamin $B_{12}$-XVI. Modification of Cyano–Cobalamin,* Biophys. Acta, vol. 73 (1940), pp. 3569–3572.
Ryel et al., *Uptake and Subcellular Distribution of Vitamin $B_{12}$ in Mouse L1210 Leukemic Lymphoblasts,* Blood, vol. 44, No. 3 (1974), pp. 427–433.
LaVan et al., *Oxygen and Wound Healing,* Clinics in Plastic Surgery, vol. 17, No. 3 (1990), pp. 463–472.
Scott, *How Nature Synthesizes Vitamin $B_{12}$—A Survey of the Last Four Billion Years,* Angewandte Chemie, vol. 32, No. 9 (1993), pp. 1223–1376.
Li et al., *Effects of Hydroxocobalamin and Haemoglobin on No–Mediated Relaxations in the Rat Anoccocygeus Muscle,* Clinical and Experimental Pharmacology and Physiology, vol. 20 (1993), pp. 633–640.
Rajanayagam et al., *Differential Effects of Hydroxocobalamin on NO–Mediated Relaxations in Rat Aorta and Anococcygeus Muscle,* J. Pharmacol. vol. 108 (1993), pp. 3–5.
King et al., *Cobalt: $B_{12}$ Enzymes & Coenzymes,* Encyclopedia Inorganic Chemistry, vol. 2 (1994), pp. 697–712.
Greenberg et al., *Hydroxocobalamin Vitamin $B_{12a}$ Prevents and Reverses Endotoxin–Induced Hypotension and Mortality in Rodents: Role of Nitric Oxide,* The Journal of Pharmacology and Experimental Therapeutics, vol. 273, No. 1 (1995), pp. 257–265.
Sagar et al., *Nitric Oxide and Anti–Cancer Therapy,* Cancer Treatment Reviews, vol. 21 (1995), pp. 159–181.
Quadros et al., *The Dynamics of Cobalamin Utilization in L–1210 Mouse Leukemia Cells: A Model of Cellular Cobalamin Metabolism,* Biochimica et Biophysica Acta 1244 (1995), pp. 395–403.
Rochelle et al., *Interactions Between Hydroxocobalamin and Nitric Oxide (NO): Evidence for a Redox Reaction Between NO and Reduced Cobalamin and Reversible NO Binding to Oxidized Cobalamin,* The Journal of Pharmacology and Experimental Therapeutics, vol. 245, No. 1 (1995), pp. 48–52.
Shabani et al., *Enhancement of Wound Repair with a Topically Applied Nitric Oxide–Releasing Polymer,* Wound Repair and Regeneration, vol. 4, No. 3 (1996), pp. 353–362.
Brouwer et al., *Nitric Oxide Interactions with Cobalamins: Biochemical and Functional Consequences,* vol. 88, No. 5 (1996), pp. 1857–1864.
Russell–Jones., Chem. Abst. 1990: 42564.

*Primary Examiner*—Mukund J. Shah
*Assistant Examiner*—Pavanaram K. Sripada
*Attorney, Agent, or Firm*—Renner, Kenner, Greive, Bobak, Taylor & Weber

[57] ABSTRACT

A purified complex of a metallocorrinoid, such as a vitamin $B_{12}$ compound, and a pharmacological agent, such as nitric oxide, that is capable of site-specific delivery of the pharmacological agent in vivo. The pharmacological agent is bound to the metallocorrinoid in a non-donating solvent. The complex is then resuspended in a biocompatible medium and inserted into the recipient. The pharmacological agent then releases in vivo, especially under acidic conditions.

17 Claims, 2 Drawing Sheets

METALLOCORRINOIDS AS BIOLOGICALLY COMPATIBLE CARRIERS OF PHARMACOLOGICAL AGENTS

TECHNICAL FIELD

The present invention generally relates to biologically compatible, metallocorrinoid carriers of pharmacological agents. More particularly, the present invention relates to a nitric oxide (NO)-substituted cobalamin. The present invention also relates to methods for site-specific delivery of nitric oxide agents using a metallocorrinoid.

BACKGROUND OF THE INVENTION

A need for the site-specific delivery of pharmacological agents is well known in many fields of medicine. When using chemotherapeutic agents, for example, a major concern is their toxicity to non-target cells. Thus, a site-specific carrier is needed that will deliver a chemotherapeutic agent capable of killing targeted cells without killing surrounding healthy cells.

NO is a good chemotherapeutic agent because intracellular concentrations of NO have been shown to be deleterious to tumor cells. In addition, NO has shown potential benefits in post-arteriosclerosis therapy, wound healing, impotence therapy, and other therapies. Site-specific delivery is often medically preferred, however, because many pharmacological agents, such as NO, can be toxic.

The wound healing process is a complicated orchestration of a series of physiological responses, including an inflammatory response, angiogenesis, the development of fibrous tissue, and re-epithelization LaVan et al., *Wound Healing*, 17 (3):463 (1990). NO is both directly and indirectly involved in each of these physiological processes. Vitamin $B_{12}$ is also known to enhance wound healing.

Vitamin $B_{12}$ compounds are naturally occurring, non-immunogenic, non-toxic vitamins that are present in the human body. Vitamin $B_{12}$ compounds are known to have many biological functions. They are required by the enzyme methionine synthase, for example, which is involved in the production of DNA. Pregnant women need increased amounts of $B_{12}$ which is involved in the production of red blood cells. It is also believed that vitamin $B_{12}$ enhances the effects of other vitamins and nutrients in tissue repair.

Currently, polymeric NONOates are growing in popularity as prospective NO donors because they are able to sustain elevated levels of NO in vivo over extended periods of time. Many polymeric NONOates, however, can be toxic. After nitric oxide release these polymers degrade, often causing an inflammatory response and other adverse tissue reactions.

Another drawback of conventional NO-donors is that they are limited in the conditions under which they can be used. These donors generally release NO without specificity under physiological conditions; thus, they release NO as soon as they enter the body. Therefore, there is a need for site-specific, biologically compatible donors of NO that have less harmful side effects.

Metallocorrinoids are corrin rings with a metal-atom center, such as Co, Fe, Ni, or Mn. A corrin ring is four reduced pyrrole rings linked together as shown in FIG. 1. A subclass of naturally occurring metallocorrinoids found in the human body is a cobalamin, that is, a cobalt-centered corrin ring. Many cobalamins related to vitamin $B_{12}$ compounds are a subclass of cobalamin that includes hydroxocobalamin, cyanocobalamin, nitrocobalamin, methylcobalamin, and 5'-deoxyadenocobalamin.

It is generally known that NO will bind to a cobalamin. Heretofore, it has been attempted to use a cobalamin, such as hydroxocobalamin, as a scavenger of NO. For example, PCT Application No. WO95/31204 (Greenburg et al.) discloses a process whereby hydroxocobalamin is added to an NO-rich site in vivo. Hydroxocobalamin then binds the NO, thereby decreasing the concentration of potentially harmful NO at the site. Heretofore, however, nitrosylcobalamin has not been synthesized, isolated, purified, or used to deliver NO.

SUMMARY OF THE INVENTION

It is therefore an object of the present invention to provide a carrier that is biologically compatible.

It is an additional object of the present invention to provide a carrier that does not effect an immune response.

It is another object of the present invention to provide a carrier that has minor or no adverse side effects in vivo.

It is still another object of the present invention to provide a method for synthesizing a hydroxocobalamin-NO complex in vitro.

It is yet a further object of the present invention to provide a purified form of a hydroxocobalamin-NO complex.

It is still another object of the present invention to provide a method of site-specific delivery of NO.

It is yet another object of the present invention to provide a method of delivering NO to a site with slow, long term delivery.

At least one or more of the foregoing objects, together with the advantages thereof over the known art relating to donors of pharmacological agents, which shall become apparent from the specification which follows, are accomplished by the invention as hereinafter described and claimed.

In general, the present invention provides a complex of a metallocorrinoid and a pharmacological agent that is capable of site-specific delivery of the pharmacological agent in vivo, comprising a complex having the general formula:

(I)

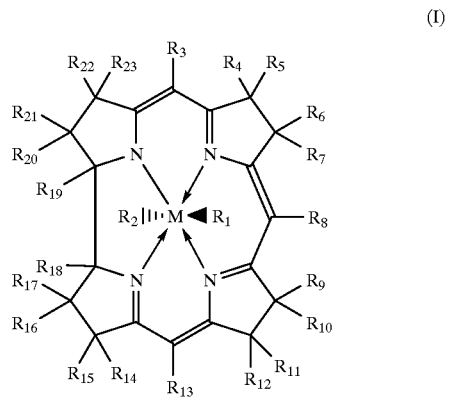

wherein $R_1$ is a pharmacological agent bound to M under physiological conditions and has at least one electron-donating group selected from the group consisting of free radicals and nucleophiles, wherein $R_2$ is selected from the group consisting of a compound having an electron-donating group, wherein $R_3$–$R_{23}$ is each independently selected from the group consisting of the pharmacological agent, hydrogen or an organic moiety consisting of aliphatic (linear or cyclic) or aromatic groups having from 1 to about 30 carbon atoms, heteroatoms, or combinations thereof, and wherein M is a transition metal selected from the group consisting of Sc, Ti, V, Cr, Mn, Fe, Co, Ni, Cu and Zn.

The present invention also provides a method for making a complex of a metallocorrinoid and a pharmacological agent comprising the steps of providing the metallocorrinoid, the pharmacological agent, and a non-donor solvent that is preferably also apolar and aprotic; contacting the metallocorrinoid, the agent and the solvent such that the agent is releasably bound to the metallocorrinoid; and eliminating the solvent, such as by evaporation. By way of example, the solvent can be methylene chloride, dichloroethane, hexane, carbon tetrachloride, benzene, chloroform, or combinations thereof.

In addition, the present invention provides a method for site-specific delivery of a pharmacological agent in vivo, comprising the steps of providing a complex of a metallocorrinoid and the pharmacological agent; and introducing the complex in vivo, wherein the pharmacological agent releases from the complex in vivo.

PREFERRED EMBODIMENT FOR CARRYING OUT THE INVENTION

Figure 1:
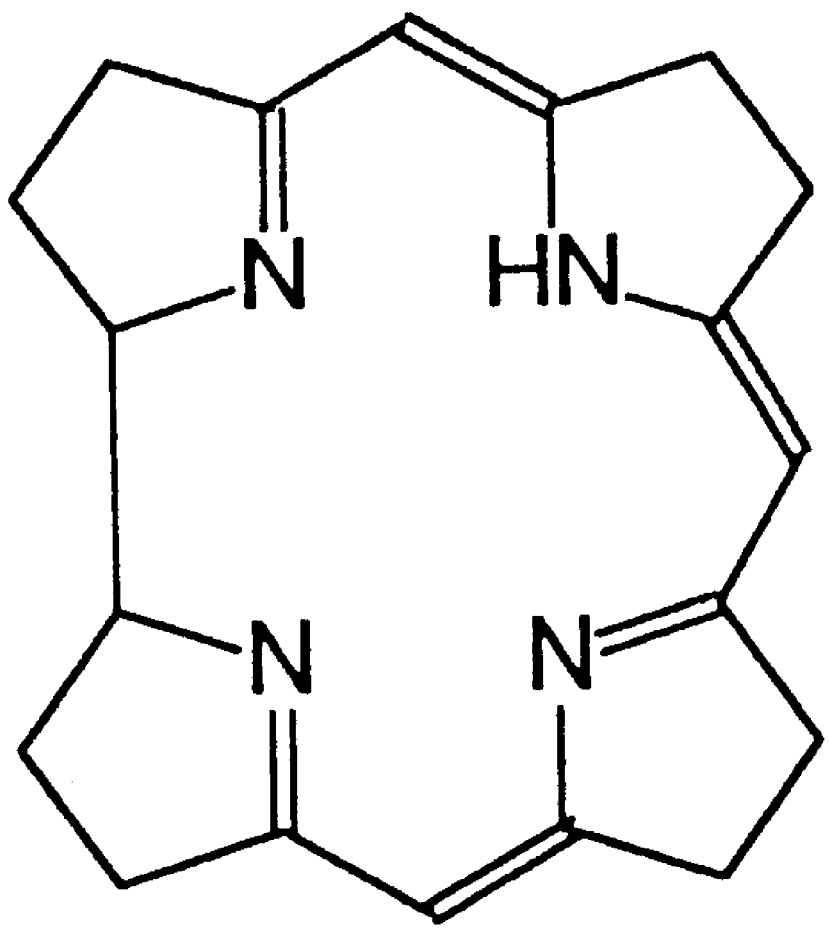
FIG. 1 is the general structure of a corrin ring.

It has now been found that a biologically compatible metallocorrinoid, acting as a carrier, can be loaded with a pharmacological agent in vitro then introduced in vivo and released. Metallocorrinoids are compounds containing a corrin ring having a transition metal center, as shown in Formula I:

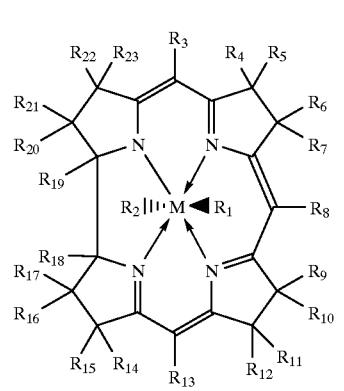

(I)

It is believed that a metallocorrinoid carrier of the present invention is most biologically compatible when $R_3$–$R_{23}$ are independently selected from the group consisting of hydrogen or organic moieties consisting of aliphatic (linear or cyclic) or aromatic groups having from 1 to about 30 carbon atoms. The organic moieties can contain heteroatoms such as nitrogen, sulfur, oxygen, or phosphorus.

Preferably, $R_4$, $R_7$, $R_{11}$, $R_{17}$, $R_{21}$, and $R_{23}$ are amides having from 1 to about 7 carbon atoms. More preferably, $R_4$, $R_{11}$, $R_{17}$, and $R_{21}$ are terminal amides with from 1 to about 4 carbon atoms, and $R_7$ and $R_{23}$ are terminal amides with from 1 to about 5 carbon atoms. $R_{15}$ is preferably an analog of 1-α-D ribofuranosyl-5,6-dimethyl benzimidazoyl-3-phosphate.

$R_1$ and $R_2$ are preferably good leaving groups because these sites are preferred loading sites for the pharmaceutical compound to be carried. It is believed that these sites are preferred because there is less steric hindrance and because the metal bonds are weaker than the bonds to the corrin ring. More preferably, at least $R_1$ is a good leaving group because it is the most preferred substitution site. By "good leaving group," it is meant that using known techniques and without undue experimentation, one of ordinary skill in the art could achieve a high level of substitution for that group with a nucleophile.

M is a transition metal selected from the group consisting of Sc, Ti, V, Cr, Mn, Fe, Co, Ni, Cu, and Zn. Preferably, M is selected from the group consisting of Cr, Mn, Fe, Co, Ni, Cu and Zn, more preferably M is Fe or Co, and most preferably M is Co.

$R_1$ and $R_2$ are shown in the β and α positions, respectively; $R_1$ extends towards the reader, perpendicular to the substantially planar ring, and $R_2$ extends away from the reader. $R_1$ and $R_2$ can be identical or different moieties. The size and nature of $R_1$ or $R_2$ is limited only by its interference in the affinity between the corrin ring and a receptor of corrin rings or by its effect on biological compatibility.

In a preferred embodiment, the metallocorrinoid of the present invention is a cobalamin. Cobalamins can be represented generally by Formula II:

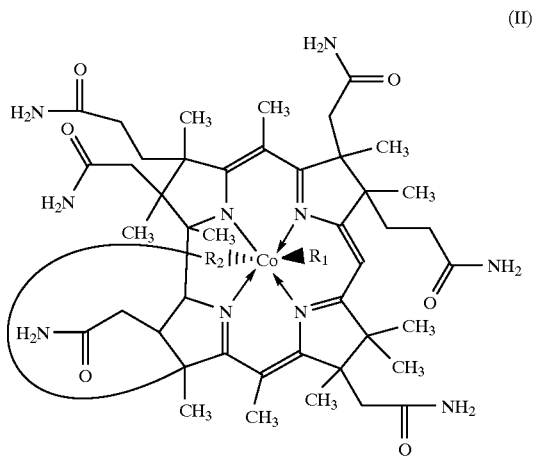

(II)

wherein $R_1$ can be any substituent that will bind to cobalt. Under appropriate conditions, such as high pressure of NO gas, $R_1$ can be displaced by a nucleophilic pharmacological agent. Preferably, $R_1$ can be selected from the group consisting of methyl, cyano, hydroxyl, aqua, and 5'-deoxyadenosyl, thereby resulting in a cobalamin that is known to be naturally occurring, such as a vitamin $B_{12}$ compound. $R_2$ is 1-α-D ribofuranosyl-5,6-dimethyl benzimidazoyl-3-phosphate.

The pharmacological agent to be loaded to the metallocorrinoid can be any agent having an electron donating group capable of binding to a metal atom, including, but not limited to, free radicals and nucleophiles. Examples of suitable electron donating groups include flavin radicals, phenyl radicals, nucleophilic alkylating agents, or hydrocarbon radicals. The size of the pharmacological agent is only limited by biological compatibility. One of ordinary skill in the the art could determine, without undue experimentation, whether a given pharmacological agent, when loaded onto the carrier of the present invention, causes the resulting complex to lose biocompatibility. Nonetheless, it is expected that a pharmacological agent with fewer than about 100 carbon atoms would retain biocompatibility. Preferably, the good pharmacological agent has fewer than about 50 carbon atoms. Therefore, there are many pharmacological agents that can be delivered according to the present invention. Many known natural and synthetic drugs, for example, can be delivered because they often contain nucleophilic moieties or atoms with lone pair electrons.

In one embodiment of the present invention, NO is loaded onto the compound shown in Formula I. "Loading," as used herein, refers to the substitution of a pharmacological agent for one or more of the chemical groups attached to a metallocorrinoid. While not intending to be bound by any particular theory, it is believed that NO will substitute preferably for $R_1$, less often for $R_2$, and much less often at other sites, such as terminal amides. If the metallocorronoid is a cobalamin, then loading of NO into the $R_1$ position, forming nitrosylcobalamin, is likely to occur.

Under acidic conditions in vivo, such as lysosomes or endosomes, the pharmacological agent releases most rapidly from the metallocorrinoid, presumably by an oxidizing agent, such as a Lewis acid. Preferably, the site of NO release contains cells with $B_{12}$ receptors. Depending on the desired application, however, affinity to the receptors may not be necessary.

Figure 2:
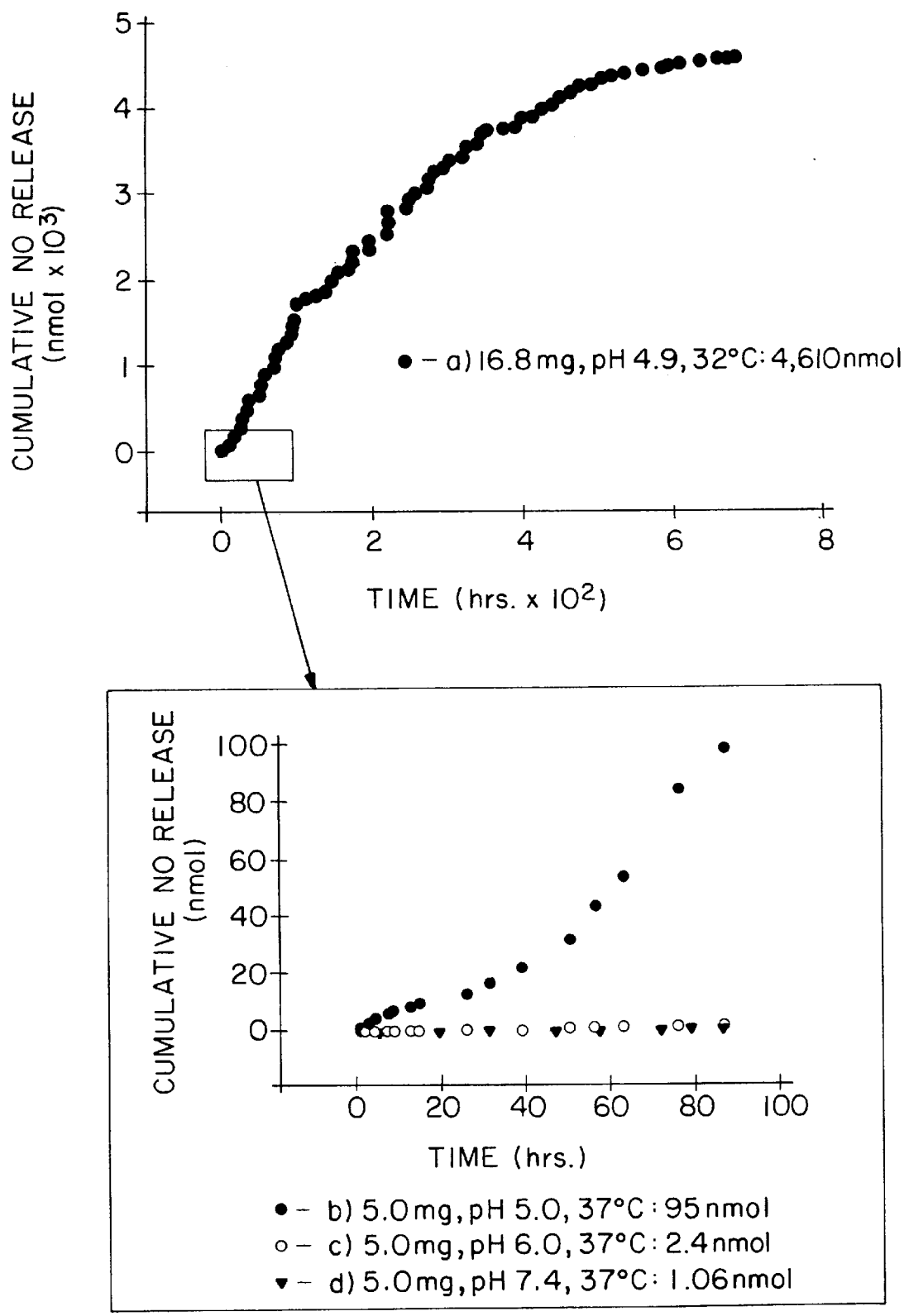
FIG. 2 shows release profiles of NO from an NO-cobalamin complex at various pH and temperature.

After loading NO to a metallocorrinoid carrier, the carrier is delivered to a site in vivo, for example, by injection, topical application or implantable pumps. Depending on the physiological conditions, the NO will release from the carrier at various rates. FIG. 2 shows the release profile of NO from nitrosylcobalamin at 32° C., pH 4.9 and at 37° C. (inset), pH 7.4, 6.0, or 5.0. Upon release of the NO in vivo, it is believed that the molecule shown in Formula II reverts to hydroxocobalamin or aquacobalamin or remains as a reduced cobalamin.

Site-specific delivery of NO can be used for various treatments, including chemotherapy, post-arteriosclerosis therapy, wound healing and impotence therapy. For example, a complex of vitamin $B_{12}$ and a chemotherapeutic agent, such as NO, may be effective in treating some types of cancer, especially those that rely on vitamin $B_{12}$ in the cell proliferation process, by releasing toxic doses of NO inside the cell. Moreover, the present invention is particularly well-suited for pharmaceutical delivery to leukemia cells because lysosomes have a pH of about 5, and it is believed that leukemia cells use a lysosomal-cellular receptor pathway. Likewise, the present invention is particularly well-suited for other $B_{12}$ pathways involving lysosomes, endosomes, or other acidic conditions. Flesh wounds, for example, typically have a pH ranging from about 4 to about 6.

Arteriosclerosis is a condition whereby a blood vessel is at least partially blocked and blood flow is diminished. Accordingly, an implanted device having an NO donor of the present invention bound to it is more effective because the release of NO causes vasodilation, thereby providing a long term dilated state or preventing the accumulation of plaque or blockage reoccurs. The NO donor of the present invention is suitable for this application for the additional reason that it has a long half-life, thereby providing long-term release. Nitrosylcobalamin, for example, has a 210-hour half-life in vitro at pH 5. The in vivo half life can be adjusted by changing the pH or by using different salts of the cobalamins or different substituents, thereby controlling NO release.

EXPERIMENTAL 500 mg samples of hydroxocobalamin, an acetate salt and a hydrochloride salt obtained from Sigma Chemical Co. (St. Louis, Mo.), were each dissolved in 100 mL methylene chloride to produce 5 mg/mL solutions. The samples of hydroxocobalamin were exposed to NO gas in a dark closed system at room temperature for at least ten days at 100 psig, as described by Shabani et al., *Wound Repair Regen* 4(3):353 (1996), incorporated herein by reference. The system was purged daily of NO gas using nitrogen and the samples were re-exposed to fresh NO gas for at least one hour at 100 psig. The system remained at 100 psig after NO exposure. After an observable color change (ten days), the methylene chloride was removed using rotary-evaporation and approximately 450 mg of a solid product was collected and stored at –6° C.

Before NO exposure, the acetate salt was dark red in color and the hydrochloride salt was violet. Upon the completion of the reaction with NO, both salts turned a brilliant orange, indicating a reduction of the $Co^{3+}$ of the original hydroxocobalamin to $Co^{2+}$ upon the binding of NO, to the cobalt, to form nitrosylcobalamin. This was confirmed by UV/VIS spectroscopy and IR spectroscopy.

The solubilities of the acetate salt and the hydrochloride salt of hydroxocobalamin after NO exposure differed considerably. The acetate nitrosylcobalamin donor was readily soluble in distilled water whereas the hydrochloride nitrosylcobalamin donor was appreciably less soluble. It is envisioned that by carefully selecting a salt of the nitrosylcobalamin, the rate of NO release can be adjusted to meet the needs of specific biomedical applications without altering the chemical makeup of the nitrosylcobalamin.

The substitution of the hydroxyl group in the beta position, for example, by an NO group on hydroxocobalamin leads to the formation of nitrosylcobalamin. Similarly, nitrosylcobalamin can be formed by the substitution of other ligands in the beta position, such as cyano in cyanocobalamin.

The nitric oxide content and kinetic release profile, shown in FIG. 2, of nitrosylcobalamin was determined in vitro using a nitrogen oxides analyzer (Monitor Labs Model 8440). The amount of NO-"loading" was determined by examining the cumulative NO release, characterized at pH 4.9, 32° C., during a time span of 675.5 hours. The total NO released was 4,610 nmol NO, 38% loading based on the theoretical maximum of 11,890 nmol. The first twenty hours of NO release was characterized in great detail, with data readings taken every 15 minutes for the first eight hours and every half hour thereafter, resulting in the production of 260 nmol NO. The cumulative NO release profile followed first order kinetics ($R^2$=0.9984) with a calculated half life of 210 hours. pH dependency was established by comparing 5 mg samples of nitrosylcobalarnin at pH 5.0, 6.0, and 7.4 (37° C.) over an 86 hour time span producing 95.0, 2.4, and 1.05 nmol of NO respectively. At pH 10.0, NO release was undetected even though the sample size was increased to 20.6 mg.

Based upon the foregoing disclosure, it should now be apparent that the use of the composition of matter and method described herein will carry out the objects set forth hereinabove. It should also be apparent to those skilled in the art that the method of the present invention can be practiced to deliver a pharmacological compound.

It is, therefore, to be understood that any variations evident fall within the scope of the claimed invention and thus, the selection of specific metallocorrinoids can be determined without departing from the spirit of the invention herein disclosed and described. Moreover, the scope of the invention shall include all modifications and variations that may fall within the scope of the attached claims.

What is claimed is:

1. A method for making a complex of a metallocorrinoid and nitric oxide comprising the steps of:

providing a metallocorrinoid, having the formula (I):

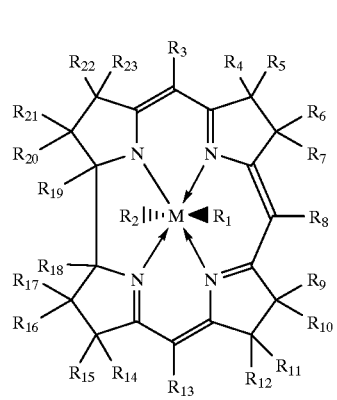

(I)

wherein M is a metal atom selected from the group consisting of Sc, Ti, V, Cr, Mn, Fe, Co, Ni, Cu, and Zn;

wherein $R_1$–$R_{23}$ are moieties independently selected from the group consisting of hydrogen, aliphatic groups having from 1 to about 30 carbon atoms, heteroatoms, or combinations thereof, aromatic groups having from 1 to about 30 carbon atoms, heteroatoms, or combinations thereof, wherein at least one of $R_1$ and $R_2$ is a good leaving group;

dissolving the metallocorrinoid in a non-donating solvent and exposing said dissolved metallocorrinoid to nitric oxide such that said good leaving group is removed and nitric oxide becomes bound to the metallocorrinoid in place of said good leaving group;

wherein nitric oxide is not released from said metallocorrinoid under physiological conditions; and wherein nitric oxide is released from said metallocorrinoid under acidic conditions.

2. The method for making a complex of a metallocorrinoid and a pharmacological agent according to claim 1, wherein $R_3$, $R_5$, $R_6$, $R_8$, $R_9$, $R_{10}$, $R_{12}$, $R_{13}$, $R_{14}$, $R_{16}$, $R_{18}$, $R_{19}$, $R_{20}$, and $R_{22}$ are independently selected from the group consisting of hydrogen and an alkyl group having from 1 to about 3 carbon atoms, $R_4$, $R_{11}$, $R_{17}$, and $R_{21}$ are independently selected from the group consisting of an amide or a carboxylic acid having from 1 to about 4 carbon atoms, $R_7$ and $R_{23}$ are independently selected from the group consisting of an amide or a carboxylic acid having from 1 to about 5 carbon atoms, and $R_{15}$ is a ring bound to $R_2$ such that $R_{15}$-$R_2$ is 1-α-D ribofuranosyl-5,6-dimethyl benzimidazoyl-3-phosphate.

3. The method for making a complex of a metallocorrinoid and nitric oxide agent according to claim 2, wherein $R_1$ is be selected from the group consisting of methyl, cyano, hydroxyl, aqua, and 5'-deoxyadenosyl.

4. The method for making a complex of a metallocorrinoid and nitric oxide agent according to claim 1, wherein the solvent is non-donating.

5. The method for making a complex of a metallocorrinoid and nitric oxide agent according to claim 1, wherein the solvent can be selected from the group consisting of a methylene chloride, dichloroethane, hexane, carbon tetrachloride, benzene, and chloroform.

6. The method for making a complex of a metallocorrinoid and nitric oxide agent according to claim 1, wherein the solvent is methylene chloride.

7. The method for making a complex of a metallocorrinoid and nitric oxide agent according to claim 1, wherein the metallocorrinoid has a metal atom selected from the group consisting of Fe, Co, Ni and Mn.

8. The method for making a complex of a metallocorrinoid and nitric oxide agent according to claim 1, wherein the metallocorrinoid has a Co atom.

9. The method for making a complex of a metallocorrinoid and nitric oxide according to claim 1, wherein the metallocorrinoid has the following structure:

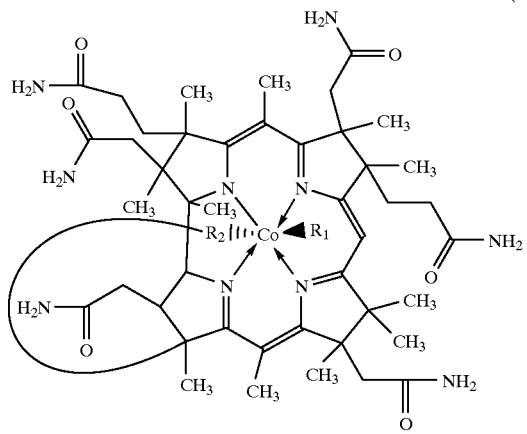

(II)

wherein $R_1$ is nitric oxide bound to cobalt by an electron donating group under physiological conditions;

wherein $R_2$ is a moiety selected from the group consisting of aliphatic groups having from 0 to about 20 carbon atoms, heteroatoms, or combinations thereof, aromatic groups having from 0 to about 20 carbon atoms, heteroatoms, or combinations thereof, and nitric oxide; and wherein $R_2$ has at least one electron-donating group.

10. The method for making a complex of a metallocorrinoid and nitric oxide according to claim 9, wherein the electron donating group can be selected from the group consisting of compounds with at least one nucleophilic moiety.

11. The method for making a complex of a metallocorrinoid and nitric oxide according to claim 9, further comprising the step of eliminating the solvent.

12. A method for site-specific delivery of nitric oxide in vivo, comprising the steps of:

making a complex of a metallocorrinoid and nitric oxide according to claim 1;

resuspending the complex in a biological compatible solvent; and introducing the complex in vivo;

wherein the nitric oxide releases from the complex in vivo under acidic conditions only.

13. A compound comprising:

a complex having the general formula (I):

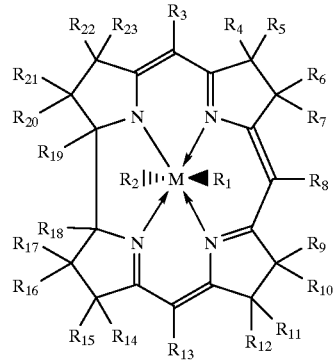

(I)

wherein M is a transition metal selected from the group consisting of Sc, Ti, V, Cr, Mn, Fe, Co, Ni, Cu and Zn;

wherein $R_1$ is nitric oxide bound to M under physiological condition wherein $R_2$ is selected from the group consisting of a compound having an electron-donating group, wherein $R_3$–$R_{23}$ is each independently selected from the group consisting of hydrogen, aliphatic groups having from 1 to about 30 carbon atoms, heteroatoms, or combinations thereof, aromatic groups having from 1 to about 30 carbon atoms, heteroatoms, nitric oxide, or combinations thereof.

14. The compound according to claim 13, wherein the complex having the formula (I) is further defined by the general formula:

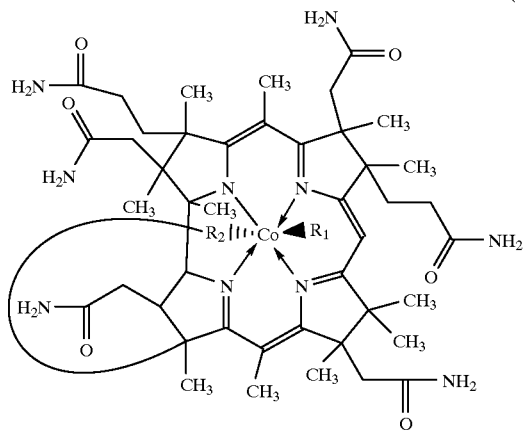

(II)

wherein $R_1$ is nitric oxide bound to cobalt by an electron donating group under physiological conditions;

wherein $R_2$ is a moiety selected from the group consisting of aliphatic groups having from 0 to about 20 carbon atoms heteroatoms, and combinations thereof, aromatic groups having from 0 to about 20 carbon atoms, heteroatoms and combinations thereof, and nitric oxide and has at least one electron-donating group;

wherein $R_2$ is a moiety selected from the group consisting of aliphatic groups having 0 to 20 carbon atoms, heteroatoms or combinations thereof, aromatic groups having 0 to 20 carbon atoms, heteroatoms, or combinations thereof and nitric oxide (NO); and wherein $R_2$ has at least one electron-donating group.

15. The compound according to claim 14, wherein $R_2$ is 1-α-D ribofuranosyl-5,6-dimethyl benzimidazoyl-3-phosphate.

16. A composition of matter comprising the compound of claim 14 and a solvent, wherein the solvent is non-donating.

17. The composition of matter according to claim 16, wherein the solvent is methylene chloride.

* * * * *

UNITED STATES PATENT AND TRADEMARK OFFICE
CERTIFICATE OF CORRECTION

PATENT NO : 5,936,082
DATED : August 10, 1999
INVENTOR(S) : Bauer

It is certified that error appears in the above-identified patent and that said Letters Patent is hereby corrected as shown below:

Column 1, line 12, delete the word "agents"

Column 8, line 2, delete the word "agent"
Column 8, line 3, delete the word "be"
Column 8, line 6, delete the word "agent"
Column 8, line 9, delete the word "agent"
Column 8, line 14, delete the word "agent"
Column 8, line 17, delete the word "agent"
Column 8, line 21, delete the word "agent"

Signed and Sealed this

Thirteenth Day of June, 2000

Q. TODD DICKINSON

*Attest:*

*Attesting Officer*     *Director of Patents and Trademarks*